US010052350B2

(12) United States Patent
Niu et al.

(10) Patent No.: US 10,052,350 B2
(45) Date of Patent: Aug. 21, 2018

(54) FABRICATION OF GELATIN HYDROGEL SHEET FOR THE TRANSPLANTATION OF CORNEAL ENDOTHELIUM

(71) Applicant: WAKE FOREST UNIVERSITY HEALTH SCIENCES, Winston-Salem, NC (US)

(72) Inventors: GuoGuang Niu, Winston-Salem, NC (US); Shay Soker, Greensboro, NC (US)

(73) Assignee: WAKE FOREST UNIVERSITY HEALTH SCIENCES, Winson Salem, NC (US)

( * ) Notice: Subject to any disclaimer, the term of this patent is extended or adjusted under 35 U.S.C. 154(b) by 0 days.

(21) Appl. No.: 14/344,011

(22) PCT Filed: Sep. 17, 2012

(86) PCT No.: PCT/US2012/055765
§ 371 (c)(1),
(2) Date: Mar. 10, 2014

(87) PCT Pub. No.: WO2013/040559
PCT Pub. Date: Mar. 21, 2013

(65) Prior Publication Data
US 2014/0377326 A1    Dec. 25, 2014

Related U.S. Application Data

(60) Provisional application No. 61/535,642, filed on Sep. 16, 2011.

(51) Int. Cl.
| | |
|---|---|
| *A61K 35/30* | (2015.01) |
| *A61L 27/22* | (2006.01) |
| *A61L 27/26* | (2006.01) |
| *A61L 27/38* | (2006.01) |
| *A61L 27/50* | (2006.01) |
| *A61L 27/52* | (2006.01) |
| *A61L 27/54* | (2006.01) |
| *A61L 27/56* | (2006.01) |
| *A61F 2/14* | (2006.01) |

(52) U.S. Cl.
CPC ............ *A61K 35/30* (2013.01); *A61L 27/222* (2013.01); *A61L 27/26* (2013.01); *A61L 27/3808* (2013.01); *A61L 27/50* (2013.01); *A61L 27/52* (2013.01); *A61L 27/54* (2013.01); *A61L 27/56* (2013.01); *A61F 2/142* (2013.01); *A61L 2300/236* (2013.01); *A61L 2430/16* (2013.01)

(58) Field of Classification Search
CPC ....... A61K 35/30; A61L 27/222; A61L 27/52; A61L 2300/236; A61F 2/142
See application file for complete search history.

(56) References Cited

U.S. PATENT DOCUMENTS

| | | | | | |
|---|---|---|---|---|---|
| 5,374,515 | A | * | 12/1994 | Parenteau | ................. A61F 2/14 435/1.1 |
| 5,382,514 | A | * | 1/1995 | Passaniti | ............ A61K 49/0004 424/520 |
| 6,458,386 | B1 | * | 10/2002 | Schacht | ................ A61L 15/225 424/426 |
| 2007/0196454 | A1 | * | 8/2007 | Stockman | ............ A61K 31/785 424/445 |
| 2008/0317818 | A1 | * | 12/2008 | Griffith | ................ A61K 9/0051 424/427 |
| 2009/0263465 | A1 | | 10/2009 | Hsiue et al. | |

OTHER PUBLICATIONS

Dabin et al. "In vitro kinetics of basic fibroblast growth factor diffusion across a reconstituted corneal endothelium". Journal of Cellular Physiology. 1991, 147: 396-402.*
Supplementary European Search Report from European Patent Application No. EP12832258, dated Mar. 25, 2015.
Ryou Watanabe et al., "A Novel Gelatin Hydrogel Carrier Sheet for Corneal Endothelial Transplantation." 2011 Tissue Engineering Part A 17(17-18):2213-19.
Hennink, W.E. et al., "Novel Crosslinking Methods to Design Hydrogels," Adv. Drug. Del. Rev., 2002, pp. 13-36. vol. 54.
Hill-West, J.L. et al., "Inhibition of Thrombosis and Intimal Thickening by in situ Photopolymerization of Thin Hydrogel Barriers," Proc. Natl. Acad. Sci. USA, 1994, pp. 5967-5971, vol. 91, No. 13.
Hoffman, A.S., "Hydrogels for Biomedical Applications," Adv. Drug Del. Rev., 2002, pp. 3-12, vol. 54, No. 1.
Hwang, N.S. et al., "Chondrogenic Differentiation of Human Embryonic Stem Cell-Derived Cells in Arginine-Glycine-Aspartate-Modified Hydrogels," Tissue Eng., 2006, pp. 2695-2706, vol. 12, No. 9.
Ifkovits, J.L. et al., "Review: Photopolymerizable and Degradable biomaterials for Tissue Engineering Applications" Tissue Eng., 2007, pp. 2369-2385, vol. 13, No. 10.
Koizumi, N. et al., "Cultivated Corneal Endothelial Cell Sheet Transplantation in a Primate Model," Invest. Opthalmol. Vis. Sci., 2007, pp. 4519-4526, vol. 48, No. 10.
Lai, J-Y. et al., "Functional Assessment of Cross-Linked Porous Gelatin Hydrogels for Bioengineered Cell Sheet Carriers,"Biomacromolecules, 2010, pp. 1387-1397, vol. 11.
Lai, J-Y. et al., "Ocular Biocompatibility of Carbodiimide Cross-Linked Hyaluronic Acid Hydrogels for Cell Sheet Delivery Carriers," Journal of Biomaterials Science, 2010, pp. 359-376, vol. 21.
Liu, W. et al., "Recombinant Human Collagen for Tissue Engineered Corneal Substituted," Biomaterials, 2008, pp. 1147-1158, vol. 29, No. 9.
Nguyen, K.T. et al., "Photopolymerizable Hydrogels for Tissue Engineering Applications," Biomaterials, 2002, pp. 4307-4314, vol. 23.

(Continued)

*Primary Examiner* — Vera Afremova
(74) *Attorney, Agent, or Firm* — Saul Ewing Arnstein & Lehr LLP; Kathryn Doyle

(57) ABSTRACT

The invention provides a corneal endothelial composition comprising a transparent hydrogel scaffold and a single layer of cultured corneal endothelial cells on the surface of the scaffold. The hydrogel scaffold I comprised of at least one biopolymer, preferably gelatin. Also provided are methods of making a corneal endothelial scaffold.

12 Claims, 12 Drawing Sheets

(56) References Cited

OTHER PUBLICATIONS

Shin, H. et al., "Biomimetic Materials for Tissue Engineering," Biomaterials, 2003, pp. 4353-4364, vol. 24.
International Search Report dated Dec. 3, 2012 for PCT/US2012/055765.

* cited by examiner

FABRICATION OF GELATIN HYDROGEL SHEET FOR THE TRANSPLANTATION OF CORNEAL ENDOTHELIUM

CROSS-REFERENCE TO RELATED APPLICATION

This application is the U.S. national phase application filed under 35 U.S.C. § 371 claiming benefit to International Patent Application No. PCT/US2012/055765, filed on Sep. 17, 2012, which is entitled to priority under 35 U.S.C. § 119(e) to U.S. Provisional Application No. 61/535,642, filed Sep. 16, 2011, each of which is hereby incorporated by reference in its entirety.

BACKGROUND OF THE INVENTION

The inner layer of the cornea is a single layer of neural crest-derived endothelial cells (CECs), which form a barrier between the cornea and the aqueous humor and transport water from the corneal stroma. CEC loss can result from eye injuries, complications from cataract surgery (pseudophakic bullous keratopathy (PBK) or aphakic bullous keratopathy (ABK)), and in an inherited condition known as Fuchs dystrophy.

These cells do not divide during adult life. Rather, existing CECs simply spread to compensate for loss or damage. When this spreading is inadequate, vision-impairing corneal opacity results.

Traditional treatment for CEC loss or damage is penetrating keratoplasty (PK), in which a full thickness cadaveric cornea is transplanted onto a recipient eye. However, a procedure known as DSEK (Descemet's Stripping and Endothelial Keratectomy) may be an option in some cases in which the corneal stroma is not scarred. In this procedure, CECs and their underlying basement membrane (Descemet's membrane) are physically removed from the recipient, and only the inner portion of a donor cadaveric cornea, including intact CECs, is transferred to the recipient eye.

More recently, the DMEK procedure (Descemet's Membrane Endothelial Keratoplasty) has been developed, in which the donor cadaveric tissue consists only of Descemet's membrane and CEC layers Cultured CECs on synthetic films is also under study. Tissue engineered scaffold coated with corneal endothelium, is an optional way to address the shortage of cornea donors. Researchers have recently reported on the fabrication of collagen sheets used as the corneal scaffold (Koizumi et al., 2007, Invest Ophthalmol Vis Sci 10 (10): 4519-26). One of drawbacks of collagen sheet is that the scaffolds have a low transparency. Chemical cross-linking of collagen solution may be a better method to fabricate scaffolds with high transparency and proper mechanical strength (Liu et al., 2008, Biomaterials 29 (9): 1147-58). However, the solubility of natural collagen is limited, resulting in a high viscous solution at a high concentration.

However, more options are needed to provide suitable restoration of the corneal endothelial cell layer, as well as the creation for tissue engineered construct for use in corneal endothelium transplantation. The present invention addresses this unmet need in the art.

SUMMARY OF THE INVENTION

The present invention provides a corneal endothelial composition comprising a hydrogel scaffold and a layer of corneal endothelial cells present on the surface of the scaffold.

In one embodiment, the hydrogel scaffold comprises at least one biopolymer, wherein the biopolymer is selected from the group consisting of hyaluronan, chitosan, alginate, collagen, dextran, pectin, carrageenan, polylysine, gelatin and agarose.

In one embodiment, the hydrogel scaffold further comprises at least one synthetic polymer, wherein the synthetic polymer is selected from the group consisting of (meth)acrylate-oligolactide-PEO-oligolactide-(meth)acrylate, poly(ethylene glycol) (PEO), poly(propylene glycol) (PPO), PEO-PPO-PEO copolymers (Pluronics), poly(phosphazene), poly(methacrylates), poly(N-vinylpyrrolidone), PL(G)A-PEO-PL(G)A copolymers, poly(ethylene imine), and poly(ethyl glycol) diacrylate.

In one embodiment, the hydrogel scaffold comprises at least one chemical cross-linking agent, wherein the chemical cross-linking agent is selected from the group consisting of glutaraldehyde, epoxides (e.g., bis-oxiranes), oxidized dextran, p-azidobenzoyl hydrazide, N-[α-maleimidoacetoxy]succinimide ester, p-azidophenyl glyoxal monohydrate, bis-[β-(4-azidosalicylamido)ethyl]disulfide, bis[sulfosuccinimidyl]suberate, dithiobis[succinimidyl proprionate, disuccinimidyl suberate, 1-ethyl-3-[3-dimethylaminopropyl]carbodiimide hydrochloride (EDC), N-hydroxysuccinimide (NHS).

In one embodiment, the hydrogel scaffold comprises EDC and NHS.

In one embodiment, the biopolymer is gelatin.

In one embodiment, the gelatin is modified with methacrylic anhydride to form gelatin methacrylate.

In one embodiment, the corneal endothelial cells are obtained from donor cornea.

In one embodiment, the hydrogel scaffold is transparent.

In one embodiment, the hydrogel comprises heparin.

The invention also provides a method of making a corneal endothelial scaffold. In one embodiment, the method comprises generating a thin hydrogel sheet, adding at least one cross-linking agent to the hydrogel sheet, and culturing corneal endothelial cells on the surface of the hydrogel sheet.

In one embodiment, the hydrogel sheet comprises at least one biopolymer, wherein the biopolymer is selected from the group consisting of hyaluronan, chitosan, alginate, collagen, dextran, pectin, carrageenan, polylysine, gelatin and agarose.

In one embodiment, the hydrogel scaffold further comprises at least one synthetic polymer, wherein the synthetic polymer is selected from the group consisting of (meth)acrylate-oligolactide-PEO-oligolactide-(meth)acrylate, poly(ethylene glycol) (PEO), poly(propylene glycol) (PPO), PEO-PPO-PEO copolymers (Pluronics), poly(phosphazene), poly(methacrylates), poly(N-vinylpryrrolidone), PL(G)A-PEO-PL(G)A-copolymers, poly(ethylene imine), and poly(ethyl glycol) diacrylate.

In one embodiment, the at least one cross-linking agent is selected from the group consisting of glutaraldehyde, epoxides (e.g., bis-oxiranes), oxidized dextran, p-azidobenzoyl hydrazide, N-[α-maleimidoacetoxy]succinimide ester, p-azidophenyl glyoxal monohydrate, bis-[β-(4-azidosalicylamido)ethyl]disulfide, bis[sulfosuccinimidyl]suberate, dithiobis[succinimidyl proprionate, disuccinimidyl suberate, 1-ethyl-3-[3-dimethylaminopropyl]carbodiimide hydrochloride (EDC), N-hydroxysuccinimide (NHS).

In one embodiment, both EDC and NHS are applied to the hydrogel sheet.

In one embodiment, the at least one biopolymer is gelatin.

In one embodiment, the gelatin is modified with methacrylic anhydride to form gelatin methacrylate.

In one embodiment, the corneal endothelial cells are obtained from donor cornea.

In one embodiment, the hydrogel sheet comprises heparin.

In one embodiment, the corneal endothelial cells are cultured in the presence of basic fibroblast growth factor (bFGF).

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 5A through 5D, is a series of image depicting the properties of the scaffold. FIG. 5A depicts the modulus; FIG. 5B depicts the tensile strain at break; FIG. 5C depicts the tensile stress at break; and FIG. 5D depicts the stress-strain plot for HA-gelatin and gelatin-PEGDA hydrogels.

FIG. 6 demonstrates how Gel-MA solution can be formed into a gel through the application of UV irradiation and how gelatin and Gel-MA can both be used in the formulation of a hydrogel scaffold with the addition of chemical cross-linking agents EDC and NHS. This scaffold can further be modified with the attachment of RGD motifs to improve cell attachment. FIG. 6 further shows images of Gel-MA comprising hydrogel scaffolds.

DETAILED DESCRIPTION

Figure 1:
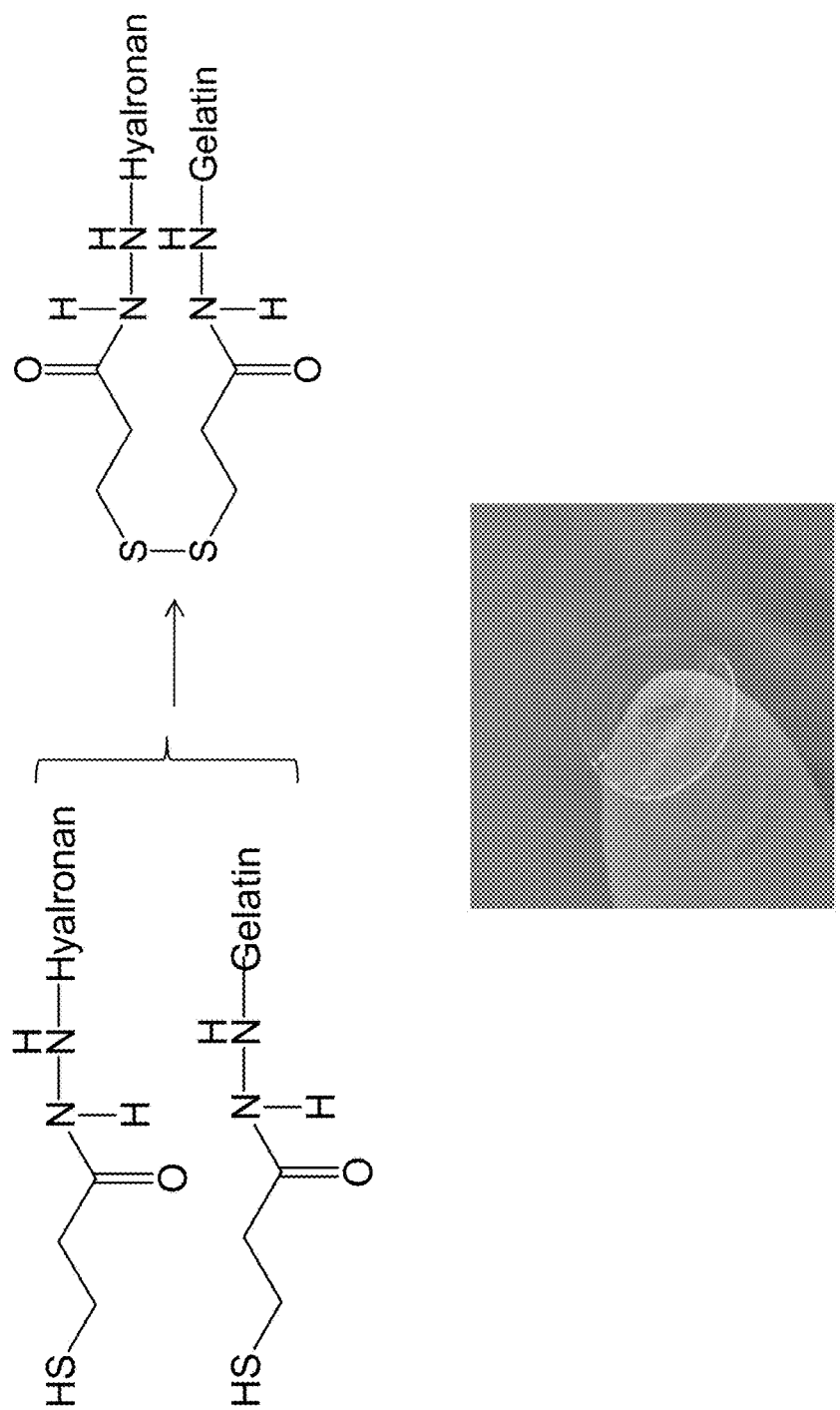
FIG. 1 is an image depicting the association of Hyalronan (HA) and gelatin in the formation of a hydrogel comprising both HA and gelatin biopolymers. An image of the resultant hydrogel scaffold is also shown.

The present invention relates generally to corneal endothelium transplantation. The corneal endothelium is the inner most layer of the cornea, and damage to this cell layer leads to cloudy and blurred vision. In one embodiment, the present invention provide compositions, and methods of making the same, comprising a transparent hydrogel scaffold, wherein the hydrogel scaffold comprises a layer of cultured corneal endothelial cells on the surface of the scaffold.

In one embodiment, the hydrogel scaffold is a sheet comprised of gelatin. In another embodiment, the hydrogel scaffold is cross-linked with at least one cross-linking agent. The ratio of gelatin to a cross-linking agent can be used to control the mechanical properties of the hydrogel scaffold. In some embodiments, the hydrogel scaffold is 95% transparent with respect to visible light, and is porous to vital nutrients. In one embodiment, the hydrogel comprises heparin. It has been discovered herein that in some instances incorporation of heparin into a gelatin hydrogel improves cell proliferation.

In one embodiment, the present invention relates to a method of fabricating a transparent hydrogel scaffold used in corneal endothelium transplantation. The method of the present invention comprises the formation of a gelatin sheet and further comprises the addition of a chemical cross-linker. An exemplary cross-linking agent can be of any type, but preferable comprises 1-Ethyl-3-[3-dimethylaminopropyl] carbodiimide hydrochloride (EDC) and N-hydroxysuccinimide (NHS).

In one embodiment, the method of the present invention comprises the culturing of corneal endothelial cells on the surface of the transparent hydrogel scaffold. In some embodiments, the cells may originate from the patient. In other embodiments, the cells may originate from donor cornea. In still other embodiments, the cells may originate from autologous or allogeneic corneal endothelial stem cells.

Following culturing of corneal endothelial cells on the transparent hydrogel scaffold of the invention, the scaffold may be inserted into the patient at the site of damaged corneal endothelium using procedures known in the art. In some embodiments, the scaffold is bioadsorbed into the natural tissue.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "as element" means one element or more than one element.

"About" as used hereto when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "autologous" is meant to refer to any material derived from the same individual.

"Allogeneic" refers to a graft derived from a different animal of the same species.

"Xenogeneic" refers to a graft derived from an animal of a different species.

As used herein "endogenous" refers so any material from of produced inside an organism, cell, tissue or system.

As used herein, tire term "exogenous" refers to any material introduced from or produced outside an organism, cell, tissue or system.

The term "scaffold" refers to a structure, comprising a biocompatible material, that provides a surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

The term "hydrogel" or "aquagel" refers to a network of oligomers or polymer chains that are water-insoluble, sometimes found as a colloidal gel in which water is the dispersion medium.

The term "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

The term "growth medium" is meant to refer to a culture medium that promotes growth of cells. A growth medium, will generally contain animal serum. In some instances, the growth medium may not contain animal serum.

The term "tissue engineering" refers to the process of generating tissues ex viva for use in tissue replacement or reconstruction. Tissue engineering is an example of "regenerative medicine," which encompasses approaches to the repair or replacement of tissues and organs by incorporation of cells, gene or other biological building blocks, along with bioengineered materials and technologies.

The term "transplanting" or "implanting" as used herein refers to the placement of a biocompatable substrate, such as a scaffold, into a subject in need thereof, with or without prior seeding and/or infiltration of cells. In some embodiments, implanting of a corneal tissue is carried out by full-thickness corneal transplantation (e.g., penetrating keratoplasty (PK)). In other embodiments, implanting is carried out using corneal endothelial keratoplasty procedures (e.g., Descemets stripping endothelial keratoplasty (DSEK), Descemets stripping automated endothelial keratoplasty (DSAEK), deep lamellar endothelial keratoplasty (DLEK). Descemet's membrane endothelial keratoplasty (DMEK), or variations thereof apparent to those of skill in the art, making use of the scaffolds described herein). As known in the art, the "cornea" is the outermost layer of the eye and is made up of substantially parallel and relatively compacted layers of tissue. Five histologically distinct layers are found: the epithelial layer, the Bowman's layer, the stroma, the Descemet's membrane, and the endothelial layer.

The terms "precursor cell," "progenitor cell," and "stem cell" are used interchangeably in the art and as used herein refer either to a pluripotent or lineage-uncommitted progenitor cell, which is potentially capable of an unlimited number of mitotic divisions to either renew itself or to produce progeny cells which will differentiate into the desired cell type. In contrast to pluripotent stem cells, lineage-committed progenitor cells are generally considered to be incapable of giving rise to numerous cell types that phenotypically differ from each other. Instead, progenitor cells give rise to one or possibly two lineage-committed cell types.

The term "Corneal tissue" as used herein is tissue isolated or harvested from the cornea. In some embodiments, corneal tissue comprises, consists of or consists essentially of tissue isolated or harvested from the stroma layer of the cornea. "Isolated" as used herein signifies that the cells are placed into conditions other than their natural environment. Tissue or cells are "harvested" when initially isolated from a subject, e.g., a primary explant. Corneal tissue "consisting essentially of" tissue isolated or harvested from the stroma layer of the cornea is 90, 95, 98, 99 or 99.5 percent or more by weight stroma and 10, 5, 2, 1 or 0.5 percent or less by weight and/or volume of non-stroma tissue, e.g., Descemet's membrane, Bowman's membrane and/or epithelial cells.

The corneal "stroma" is the thickest layer of the cornea (approximately 90% of the cornea thickness), composed of parallel collagen fibers (mostly type I and type VI) and sparse keratocytes, and lies between the Bowman's membrane and the Descemet's membrane.

"Corneal endothelial cells" or "CECs" are cells possessing the characteristics of endothelial cells normally found in the corneal endothelial cell layer. They are distinguished from other endothelial cells by the expression of both endothelial and epithelial markers, namely, one or more of the following: Zona occludin-1 (ZO-1), Na+/K+ ATPase, connexin-43, AE1/AE3, von Willebrand factor (vWF), and VE-Cadherin, but do not express CD31. In addition, CECs possess the functional abilities to 1) form a single-cell thick layer ("monolayer") on the inner surface of the cornea in a hexagonal pattern, 2) form a barrier between the cornea and the aqueous humor of the eye and regulate water flow therebetween, and 3) pump excess liquid from the cornea into the aqueous humor. In some embodiments, cells are isolated or harvested from the corneal endothelial layer. In some embodiments, CEC are derived from corneal progenitor cells (e.g., isolated or harvested from the corneal limbus). In some embodiments, CECs are isolated or harvested from the posterior surface of the peripheral cornea and limbus (e.g., strip the endothelium, and Descemet's membrane from the posterior cornea and place into collagenase to free the cells from the Descemet's membrane).

"Cultured" cells are isolated from tissue and expanded in controlled conditions known the art (e.g., 37° C., 5% $CO_3$), usually in a culture vessel. The "primary culture" is the first culture to become established after seeding disaggregated cells or primary explants into a culture vessel. "Expanding" as used herein refers to an increase in number of viable cells.

Expanding may be accomplished by, e.g., "growing" the cells through one or more cell cycles, wherein at least a portion of the cells divide to produce additional cells.

"Passaged in vitro" or "passaged" refers to the transfer or subculture of a cell culture to a second culture vessel, usually implying mechanical or enzymatic disaggregation, reseeding, and often division into two or more daughter cultures, depending upon the rate of proliferation. If the population is selected for a particular genotype or phenotype, the culture becomes a "cell strain" upon subculture, i.e., the culture is homogeneous for one or more desirable characteristics.

In some embodiments, harvested cells are not passaged. In other embodiments, cells are passaged once, twice, or three times. In still other embodiments, cells are passaged more than 3 times. In some embodiments, cells are passaged 0 to 1, 0 to 2 or 0 to 3 times. In some embodiments, cells are passaged 1 to 2, 1 to 3, or 1 to 4 or more times. In some embodiments, cells are passaged 2 to 3 or 2 to 4 or more times. In further embodiments, cells are passaged 5, 8, 10, 12 or 15 or more times. In some embodiments, cells are passaged 0, 1, 2, 3 or 4 to 8, 10, 15 or 20 or more times.

Alternatively, in other embodiments, cells are cultured to produce cell lines, which may later be differentiated to produce more specialized cells. The establishment of "cell lines," as opposed to cell strains, are by and large undifferentiated, though they may be committed to a particular lineage. Propagation naturally favors the proliferative phenotype, and in some embodiments cells may require a reinduction of differentiation by, e.g., alteration of the culture conditions. There are a number of differentiation factors known in the art that may induce differentiation in cell lines (e.g., cytokines such as epimorphin and HGF, vitamins, etc.).

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

The terms "patient," "subject" "individual," and the like aroused interchangeably herein, and refer to any animal, or cells thereof whether in vitro or in situ, amenable to the methods described herein. In certain non-limiting embodiments, the patient, subject or individual is a human.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

The phrase "therapeutically effective amount," as used herein, refers to an amount that is sufficient or effective to prevent or treat (delay or prevent the onset of, prevent the progression of, inhibit, decrease or reverse) a disease or condition, including alleviating symptoms of such diseases.

Ranges throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well, as individual numbers within that range, for example, 1, 2, 2, 7, 3, 4, 5, 5.3, and 6. This applies regardless of the breadth of the range.

DESCRIPTION

The present invention relates to novel tissue engineered constructs useful for corneal endothelium transplantation. In one embodiment, the present invention provides compositions for a transparent hydrogel scaffold, and methods of making the same. In the preferred embodiment, the transparent hydrogel comprises gelatin and further comprises a cross-linking agent. In other embodiments, the transparent hydrogel scaffold is cultured with corneal endothelial cells. The present invention is useful for replacing or repairing damaged corneal endothelium in a mammal.

Hydrogels

The present invention provides compositions comprising a transparent hydrogel scaffold, and methods of making the transparent hydrogel scaffold, for corneal endothelium transplantation. Hydrogels can generally absorb a great deal of fluid and, at equilibrium, typically are composed of 60-90% fluid and only 10-30% polymer. In a preferred embodiment, the water content of hydrogel is about 70-80%. Hydrogels are particularly useful due to the inherent biocompatibility of the cross-linked polymeric network (Hill-West, et al., 1994, Proc. Natl. Acad. Sci. USA 91:5967-5971). Hydrogel biocompatibility can be attributed to hydrophilicity and ability to imbibe large amounts of biological fluids (Brannon-Peppas. Preparation and Characterization of Cross-linked Hydrophilic Networks in Absorbent Polymer Technology, Brannon-Peppas and Harland, Eds. 1990, Elsevier: Amsterdam, pp 45-66: Peppas and Mikos. Preparation Methods and Structure of Hydrogels in Hydrogels in Medicine and Pharmacy, Peppas, Ed. 1986, CRC Press: Boca Raton, Fla., pp 1-27). The hydrogels can be prepared by crosslinking hydrophilic biopolymers or synthetic polymers. Examples of the hydrogels formed from physical or chemical crosslinking of hydrophilic biopolymers, include but are not limited to, hyaluronans, chitosans, alginates, collagen, dextran, pectin, carrageenan, polylysine, gelatin or agarose, (see: W. E. Hennink and C. F. van Nostrum, 2002, Adv. Drug Del. Rev. 54, 13-36 and A. S. Hoffman, 2002, Adv. Drug Del. Rev. 43, 3-12). These materials consist of high-molecular weight backbone chains made of linear or branched polysaccharides or polypeptides. Examples of hydrogels based on chemical or physical crosslinking synthetic polymers include but are not limited to (meth)acrylate-oligolactide-PEO-oligolactide-(meth)acrylate, poly(ethylene glycol) (PEO), poly(propylene glycol) (PPO), PEO-PPO-PEO copolymers (Pluronics), poly(phosphazene), poly(methacrylates), poly(N-vinylpyrrolidone), PL(G)A-PEO-PL(G)A copolymers, poly(ethylene imine), etc. (see A. S Hoffman, 2002 Adv. Drug Del. Rev, 43, 3-12). In some embodiments, the transparent, hydrogel scaffold comprises polyethylene glycol) diacrylate (PEGDA).

In the preferred embodiment, the transparent hydrogel scaffold comprises gelatin. Of importance in the hydrogel scaffold of the present invention is the requirement for optical transparency, as the hydrogel scaffold is used in a method of corneal endothelium transplantation. Researchers have recently reported on the fabrication of collagen sheets used as the corneal scaffold (Koizumi et al., 2007, Invest Ophthalmol Vis Sci 10 (10): 4519-26). One of drawbacks of collagen sheet is that the scaffolds have a low transparency. Chemical cross-linking of collagen solution may be a better method to fabricate scaffolds with high transparency and proper mechanical Strength (Liu et al., 2008, Biomaterials 29 (9): 1147-58). However, the solubility of natural collagen is limited, resulting in a high viscous solution at a high concentration. Gelatin is an irreversible hydrolysed form of collagen, and has been, extensively used in medical field. Compared with collagen, gelatin is cheaper and can be more easily dissolved in aqueous solution. In the preferred embodiment, the hydrogel is 95% transparent within the visible light scope. Hydrogels comprised of gelatin have a porous structure, helpful for the diffusion of nutrients and metabolites between the cornea and anterior chamber. In the preferred embodiment, the pore size is about 20-30 µm.

In some embodiments, the transparent hydrogel comprises at least one biopolymer. In other embodiments, the transparent hydrogel scaffold comprises at least two biopolymers. In yet other embodiments, the transparent hydrogel scaffold comprises at least one biopolymer and at least one synthetic polymer. In some embodiments, the transparent hydrogel comprises modified gelatin. In these embodiments, gelatin may be modified, for example, with methacrylic anhydride (MA), to produce Gelatin methacrylate (Gel-MA).

Hydrogels closely resemble the natural living extracellular matrix (Ramer and Hoffman. Synthetic Hydrogels for Biomedical Applications in Hydrogels for Medical and Related Applications, Andrade, Ed. 1976, American Chemical Society: Washington, D.C., pp 1-16). Hydrogels can also be made degradable in vivo by incorporating PLA, PLGA or PGA polymers. Moreover, hydrogels can be modified with fibronectin, lamminin, vitronectin, or, for example, RGD for surface modification, which can promote cell adhesion and proliferation (Heungsoo Shin, 2003, Biomaterials 24:4353-4364; Hwang et al., 2006 Tissue Eng. 12:2695-706). Indeed, altering molecular weights, block structures, degradable linkages, and cross-linking modes can influence strength, elasticity, and degradation properties of the instant hydrogels (Nguyen and West, 2002, Biomaterials 23 (22):4307-14; Ifkovits and Burkick, 2007, Tissue Eng. 13 (10):2369-85).

Hydrogels can also be modified with functional groups for covalently attaching a variety of proteins (e.g., collagen) or compounds such, as therapeutic agents. Therapeutic agents which can be linked to the matrix include, but are not limited to, analgesics, anesthetics, antifungals, antibiotics, anti-inflammatories, anthelminties, antidotes, antiemetics, antihistamines, antihypertensives, antimalarials, antimicrobials, antipsychotics, antipyretics, antiseptics, antiarthritics, antituberculotics, antitussives, antivirals, cardioactive drugs, cathartics, chemotherapeutic agents, a colored or fluorescent imaging agent, corticoids (such as steroids), antidepressants, depressants, diagnostic aids, diuretics, enzymes, expectorants, hormones, hypnotics, minerals, nutritional supplements, parasympathomimetics, potassium supplements, radiation sensitizers, a radioisotope, sedatives, sulfonamides, stimulants, sympathomimetics, tranquilizers, urinary antiinfectives, vasoconstrictor, vasodilators, vitamins, xanthine derivatives, and the like. The therapeutic agent can also be other small organic molecules, naturally isolated entities or their analogs, organometallic agents, chelated metals or metal salts, peptide-based drugs, or peptidic or non-peptidic receptor targeting or binding agents. It is contemplated that linkage of the therapeutic agent to the matrix, can be via a protease sensitive linker or other biodegradable linkage. Molecules which can be incorporated, into the hydrogel matrix include, but are not limited to, vitamins and other nutritional supplements; glycoproteins (e.g., collagen); fibronectin; peptides and proteins; carbohydrates (both simple and/or complex); proteoglycans; antigens; oligonucleotides (sense and/or antisense DNA and/or RNA); antibodies (for example, to infectious agents, tumors, drugs or hormones); and gene therapy reagents.

In one embodiment, the hydrogel comprises molecules that aid in the growth, and proliferation of a cell population, when cultured in or on the hydrogel. Non-limiting examples of such molecules can include proteins, peptides, supplements, small molecule inhibitors, glycosaminoglycans, growth factors, nucleic acid sequences, and combinations thereof. These molecules may have any activity that would promote cell proliferation on the hydrogel. For example, the hydrogel can comprise extracellular matrix proteins, or fragments thereof, that promote cell attachment. In one embodiment, the hydrogel comprises heparin. It is presented elsewhere herein, that incorporation of heparin into a gelatin hydrogel enhances hCEC proliferation. In one embodiment, heparin is present in the hydrogel in the range of about 0% to about 100%. In another embodiment, heparin is present in the hydrogel in the range of about 0.1% to 10%. In another embodiment, heparin is present in the hydrogel in the range of about 0.5% to 5%. In another embodiment, heparin is present in the hydrogel in the range of about 1% to about 2%.

In certain embodiments, one or more multifunctional cross-linking agents may be utilized as reactive moieties that covalently link biopolymers or synthetic polymers. Such bifunctional cross-linking agents may include glutaraldehyde, epoxides (e.g., bis-oxiranes), oxidized dextran, p-azidobenzoyl hydrazide, N-[α-maleimidoacetoxy]succinimide ester, p-azidophenyl glyoxal monohydrate, bis-[β-(4-azidosalicylamido)ethyl]disulfide, bis[sulfosuccinimidyl]suberate, dithiobis[succinimidyl proprionate, disuccinimidyl suberate, 1-ethyl-3-[3-dimethylaminopropyl]carbodiimide hydrochloride (EDC), N-hydroxysuccinimide (NHS) and other bifunctional cross-linking reagents known to those skilled in the art.

In the preferred embodiment, the method of making a transparent hydrogel scaffold comprises the addition of EDC, NHS, or both as cross-linking agents. It should be appreciated by those in skilled in the art that the mechanical properties of the hydrogel are greatly influenced by the cross-linking time and the amount of cross-linking agents.

In another embodiment utilizing a cross-linking agent, polyacrylated materials, such as ethoxylated (20) trimethylpropane triacrylate, may be used as a non-specific photoactivated cross-linking agent. Components of an exemplary reaction mixture would include a thermoreversible hydrogel held at 39° C., polyacrylate monomers, such as ethoxylated (20) trimethylpropane triacrylate, a photo-initiator, such as cosin Y, catalytic agents, such as 1-vinyl-2-pyrrolidinone, and triethanolamine. Continuous exposure of this reactive mixture to long-wavelength light (>49B nm) would produce a cross-linked hydrogel network The stabilized cross-linked hydrogel matrix of the present invention may be further stabilized and enhanced through the addition of one or more enhancing agents. By "enhancing agent" or "stabilizing agent" is intended any compound added to the hydrogel matrix, in addition to the high molecular weight components, that enhances the hydrogel matrix by providing further stability or functional advantages. Suitable enhancing agents, which are admixed with the high molecular weight components and dispersed within the hydrogel matrix, include many of the additives described earlier in connection with the thermoreversible matrix discussed above. The enhancing agent can include any compound, especially polar compounds, that, when incorporated into the cross-linked hydrogel matrix, enhance the hydrogel matrix by providing further stability or functional advantages.

Preferred enhancing agents for use with the stabilized cross-linked hydrogel matrix include polar amino acids, amino acid analogues, amino acid derivatives, intact collagen, and divalent cation chelators, such as ethylenediaminetetraacetic acid (EDTA) or salts thereof. Polar amino acids are intended to include tyrosine, cysteine, serine, threonine, asparagine, glutamine, aspartic acid, glutamic acid, arginine, lysine, and histidine. The preferred polar amino acids are L-cysteine, L-glutamic acid, L-lysine, and L-arginine. Suitable concentrations of each particular preferred enhancing agent are the same as noted above in connection with the thermoreversible hydrogel matrix. Polar amino acids, EDTA, and mixtures thereof, are preferred enhancing agents. The enhancing agents can be added to the matrix composition before or during the crosslinking of the high molecular weight components.

The enhancing agents are particularly important in the stabilized cross-linked bioactive hydrogel matrix because of the inherent properties they promote within the matrix. The hydrogel matrix exhibits an intrinsic bioactivity that will become more evident through the additional embodiments described hereinafter. It is believed the intrinsic bioactivity is a function of the unique stereochemistry of the cross-linked macromolecules in the presence of the enhancing and strengthening polar amino acids, as well as other enhancing agents.

Anatomy of the Eye

The present invention is directed towards a transparent hydrogel scaffold, and methods of making said hydrogel scaffold, wherein the said hydrogel scaffold is used in corneal endothelium transplantation. The structure of the mammalian eye can be divided into three main layers or tunics: the fibrous tunic, the vascular tunic, and the nervous tunic. The fibrous tunic, also known as the tunica, fibrosa oculi, is the outer layer of the eyeball, consisting of the cornea and sclera. The sclera is the supporting wall of the eye and gives the eye most of its white color. It is extends from the cornea (the clear from section of the eye) to the optic nerve at the back of the eye. The sclera is a fibrous, elastic and protective tissue, composed of tightly packed collagen fibrils, containing about 70% water.

Overlaying the fibrous tunic is the conjunctiva. The conjunctiva is a membrane that covers the sclera (white part of the eye) and lines the inside of the eyelids. It helps lubricate the eye by producing mucus and tears, although a smaller volume of tears than the lacrimal gland. The conjunctiva is typically divided into three parts: (a) Palpebral or tarsal conjunctivam which is the conjunctiva lining the eyelids; the palpebral conjunctiva is reflected at the superior fornix and the inferior fornix to become the bulbar conjunctiva, (b) Fornix conjunctiva: the conjunctiva where the inner part of the eyelids and the eyeball meet, (c) Bulbar or ocular conjunctiva: The conjunctiva covering the eyeball, over the sclera. This region of the conjunctiva is bound tightly and moves with the eyeball movements.

The conjunctiva effectively surrounds, covers, and adheres to the sclera. It is has cellular and connective tissue, is somewhat elastic, and can be removed, teased, away, or otherwise taken down to expose a surface area of the sclera. As explained below, it can be removed or used in conjunction with transcleral drug delivery schemes.

The vascular tunic, also known as the tunica vasculosa oculi, is the middle vascularized layer which includes the iris, ciliary body, and choroid. The choroid contains blood vessels that supply the retinal cells with oxygen and remove the waste products of respiration.

The nervous tunic, also known as the tunica nervosa oculi, is the inner sensory which includes the retina. The retina contains the photosensitive rod and cone cells and associated neurons. The retina is a relatively smooth (but curved) layer, it does have two points at which it is different; the fovea and optic disc. The fovea is a dip in the retina directly opposite the lens, which is densely packed with cone cells. The fovea is part of the macula. The fovea is largely responsible for color vision in humans, and enables high acuity, which is necessary in reading. The optic disc is a point on the retina where the optic nerve pierces the retina to connect to the nerve cells on its inside.

The mammalian eye can also be divided into two main segments: the anterior segment and the posterior segment. The anterior segment consists of an anterior and posterior chamber. The anterior chamber is located in front of the iris and posterior to the corneal endothelium and includes the pupil, iris, ciliary body and aqueous fluid. The posterior chamber is located posterior to the iris and anterior to the vitreous face where the crystalline lens and zonules fibers are positioned between an anterior and posterior capsule in an aqueous environment.

The cornea and lens help to converge light rays to focus onto the retina. The lens, behind the iris, is a convex, springy disk which focuses light, through the second humour, onto the retina, it is attached to the ciliary body via a ring of suspensory ligaments known as the Zonule of Zinn. The ciliary muscle is relaxed to focus on an object far away, which stretches the fibers connecting it with the lens, thus flattening the lens. When the ciliary muscle contracts, the tension of the fibers decreases, which brings the lens back to a more convex and round shape. The iris, between the lens and the first humour, is a pigmented ring of fibrovascular tissue and muscle fibers. Light must first pass through the center of the iris, the pupil. The size of the pupil is actively adjusted by the circular and radial muscles to maintain a relatively constant level of light entering the eye.

Light enters the eye, passes through the cornea, and into the first of two humors, the aqueous humour. Approximately two-thirds of the total eyes refractive power comes from the cornea which has a fixed curvature. The aqueous humor is a clear mass which connects the cornea with the lens of the eye, helps maintain the convex shape of the cornea (necessary to the convergence of light at the lens) and provides the corneal endothelium with nutrients.

The posterior segment is located posterior to the crystalline lens and in front of the retina. It represents approximately two-thirds of the eye that includes the anterior hyaloid membrane and all structures behind it the vitreous humor, retina, c. and optic nerve. On the other side of the lens is the second humour, the vitreous humour, which is bounded on all sides: by the lens, ciliary body, suspensory ligaments and by the retina. It lets light through without retraction, helps maintain the shape of the eye and suspends the delicate lens.

The human cornea is comprised of three layers. The outer layer is known as the epithelial layer. The middle layer is the stromal layer and comprises about 90% of the total thickness. The inner layer is the endothelial layer and comprises a single layer of thousands of small pump cells. These cells sit on a thin strip of tissue known as Descemet's membrane. These endothelial pump cells pump fluid out of the cornea so it can remain clear and thin to ensure good vision. If the pump cells stop working, the cornea fills up with fluid, becomes swollen and cloudy, and causes blurry vision.

Endothelial cells can be lost due to aging, inherited diseases (such as Fuchs' Corneal Dystrophy), trauma, and previous intraocular surgery. If a critical number of endothelial cells are lost, the cornea becomes swollen and cloudy. Generally, medical treatment is not helpful, and a corneal transplant operation is needed. The other corneal layers, the stroma and outer epithelium, are most often healthy. Many patients needing corneal transplant surgery have problems only with the endothelial cells. The present invention is directed towards a transparent hydrogel scaffold, wherein the scaffold is cultured with corneal endothelial cells ex vivo, and used in a method of corneal endothelial transplantation.

Cell Harvest, Culture and Seeding

In some embodiments, human CECs are harvested from the cornea of the patient or from an appropriate donor using methods known in the art. For example, the Descemet's membrane and the endothelial cell layer of the corneal tissue are peeled off from the corneal stroma, then transferred to a culture dish and treated with collagenase or dispase to separate the CECs from the Descemet's membrane (this may be aided mechanically by gentle pipetting). The Descemet's membrane is removed, and the CECs are cultured in an appropriate culture solution. The culture solution can be, for example, DMEM (Dullbecco's Modified Eagle's Medium) to which FBS (fetal bovine serum), b-FGF (basic-fibroblast growth factor), EGF (epidermal growth factor), insulin and antibiotics such as penicillin and streptomycin are added. A culture container (culture dish) may be used in which the surface is coated with type I collagen, type IV collagen, fibronectin, laminin and/or extracellular matrix of bovine endothelial cells, to promote cell attachment.

In some embodiments, harvested corneas are placed in a dish containing 0.02 g collagenase II in 10 mL PBS and incubated at 37° C. for 90 minutes. Sterile forceps and a spatula are then used to gently scrape the scleral rim of Descemet's membrane with intact endothelium. Cells removed by this process are centrifuged for 5 minutes at 1500 rpm and then resuspended in 2.5 mL EGM-2 complete culture medium containing 10% FBS and plated in the wells of a 6-well tissue culture dish. In some embodiments, EGM-2 may be supplemented with growth factors, antibiotics, etc., as desired. For example, EMG-2 supplemented with epidermal growth factor (EGF), insulin-like growth factor (IGF), vascular endothelial growth factor (VEGF), fibroblast growth factor (FGF), hydrocortisone, gentamicin, amphotericin-B, etc., or combinations thereof may be used. According to some embodiments, CECs cultured in petri plates with no coating, fibronectin coating, or collagen type IV coating can be used. Subculturing may be performed by enzymatic treatment (e.g., 0.05% trypsin-EDTA (Gibco)) of the cells followed by reseeding (e.g., at a density of approximately 3500 cells/cm$^2$).

In some embodiments, Descemet's membrane and endothelium are stripped from the cornea using fine forceps, a spatula and/or a bent needle under a surgical microscope, and the endothelium, alone, is digested prior to seeding the culture plate, to minimize the growth of unwanted cells (mainly fibroblasts) in the culture.

In some embodiments, after the corneal endothelial cells used for culture are expanded, a subculture of the cells is carried out when cells become subconfluent or confluent. The subculture may be carried out as known in the art. For example, cells are detached from the surface, of the culture container by treating with trypsin-EDTA and then collected. Culture solution is added to the collected cells to create a cell suspension. Centrifugation can be carried out when or after cells have been collected to provide a high cell density of cells. Common conditions for centrifugation include 500 rpm (30 g) to 1000 rpm (70 g) and 1 to 10 minutes.

As in the above-mentioned initial culture, a cell suspension can be plated on the culture container and cultured. The subculture can be carried out in the same culture conditions as the above-mentioned initial culture. The culture time may differ depending upon the cells used, but is generally 7 to 21 days. By repeating the subcultures, the number of cells can be increased and a cell suspension with a high cell density can be prepared.

The cell suspension may be seeded onto a scaffold and optionally further cultured on the scaffold. The number of cells may be adjusted so that a cell layer with a desired cell density can be formed for implantation. In some embodiments, 3000 cells/mm$^2$ to 7500 cells/mm$^2$ or 5000 cells/mm$^2$ is 7500 cells/mm$^2$ are plated so that a cell layer with a cell density of about 2000 cells/mm$^2$ to 4000 cells/mm$^2$ is formed. The culture may be carried out under the same conditions as in the above-mentioned initial culture. Seeding of the corneal endothelial cells on the scaffold can be carried out, for example, by the following procedures. First, a container with a bottom face made of membrane with a suitable pore size through which culture solution can pass (hereafter referred to as a "culture insert") is placed with the bottom face faced downward. A scaffold as described herein may then be placed on the bottom face of the culture insert (drying treatment may be carried out once in this state), then setting this culture insert in a culture container, and finally plating and culturing the cell suspension. An example of a membrane that can be used for the bottom face of the culture insert includes a commercially available polycarbonate or polyester membrane, having a pore size of about 0.4 µm to 3.0 µm. Centrifugation (e.g., 500 rpm (30 g) to 1,000 rpm (70 g) and 1 to 10 minutes) may be carried out after the cell suspension is plated in the culture insert to increase the cell density on the scaffold and promote adhesion.

In further embodiments, cultured CECs can be plated onto dishes in a DMEM-F12 medium containing 10% FCS, 5% CS, 5% Dextran, 300 pg/ml glutamine, 2.5 µg/ml Amphotericin B, and 50 ng/ml bFGF. At confluency, (7 to 10 days post seeding), the dishes are treated with 20 mM NH$_4$OH at a volume sufficient to cover at least ⅔ of the plate. After 5 minutes of shaking in a mechanical shaker, the NH$_4$OH is aspirated and the dish rinsed 5 times with PBS. Laminin and fibronectin is dissolved in distilled water at a concentration of 100 µg/ml. Type IV collagen is dissolved in 0.6% v/v acetic acid/water. Laminin, fibronectin, and type IV collagen are added to the ECM plates as needed for culture purposes.

In some embodiments, a cloning ring or cloning cylinder is used to hold the cell suspension on the scaffold, keeping the cell suspension from flowing away from the scaffold during seeding. In some embodiments, prior to seeding the cells onto the implant, one or more attachment proteins selected from fibronectin (e.g., ranging from 0.1 µg to 500 µg/ml in PBS), laminin (e.g., 0.1 µg to 500 µg/ml in PBS), RGDS (e.g., 0.01 µg to 100 82 g/ml in PBS), collagen type IV (e.g., ranging from 0.1 µg to 1000 µg in 0.1 M acetic acid) is added to the scaffold surface and incubated at 4° C. for a period ranging from 5 to 60 minutes. The residual proteins are removed after the incubation period, and the scaffold is rinsed (e.g., three times with PBS) and optionally placed on a concave holder.

In some embodiments, cultured human endothelial cells can be removed from the tissue culture dish with 0.05% trypsin and 0.02% EDTA in saline solution. The cell suspension may be counted according to methods known in the art, e.g. with a Coulter Particle Counter (Z1 model, Beckman-Coulter), and a preparation of about 50,000 to 500,000 cells/ml, or about 200,000 cells in 200 µl of culture medium (DME-H16 with 5% fetal calf serum or a serum-free medium containing a mixture of attachment proteins such as fibronectin, laminin, and fibroblast growth factors (at 10 ng to 400 ng/ml) may be added carefully onto the scaffold. Culturing of the cell comprising scaffold may be done in any conditions that promote growth and proliferation of the cell population. In some instances it may be beneficial to culture the cells in a serum free state. In one embodiment, the cell comprising scaffold is cultured in a media comprising about 0.1% to 20% FBS. In another embodiment the media comprises about 1% to 10% FBS. In another embodiment, the media comprises about 2% to 5% FBS. In some instances, the cells are cultured in the presence of growth factors. Non-limiting examples of growth factor families include epidermal growth factor (EGF), fibroblast growth factor (FGF), hepatocyte growth factor (HGF), insulin-like growth factor (IGF), nerve growth factor (NGF), and platelet derived growth factor (PDGF). In one embodiment, the CEC comprising scaffold of the invention are cultured in the presence of basic fibroblast growth factor (bFGF). A layer of 1% sodium hyaluronate, such as Healon™ (Advanced Medical Optics, Santa Ana, Calif.) at approximately 0.1 to 0.5 ml, may be layered onto the cell suspension as a protectant. The scaffold can then be incubated, at 37° C., in a 10% $CO_2$ incubator for a period of 10 minutes up to 24 hours. Alternatively, the coated scaffold will be incubated for 20 minutes and the cornea will be rinsed three times with PBS at 25° C. and ready for implantation.

Further methods of CEC cell culture are found in U.S. Patent Application Publication Nos. 2007/0275365 to Lui and 2005/0214259 to Sano et al., which are incorporated herein by reference.

Cultivation in the above-mentioned manner affords a corneal endothelial preparation wherein a corneal endothelial cell layer cultured in vitro is formed on a substrate.

The preparation of the present invention may contain a carrier to maintain good viability of the corneal endothelial cells before transplantation. Examples of the carrier include a corneoscleral graft preservation solution. (Optisol GS™), an eye ball preservation solution for corneal transplantation (EPII™) saline, phosphate buffered saline (PBS) and the like.

The scaffold of the present invention can be used as a graft for the treatment of a disease requiring a corneal endothelial transplantation, for example, bullous keratopathy, corneal edema, corneal leukoma and corneal endothelial inflammation, particularly, corneal dystrophy, bullous keratopathy caused by corneal endothelial disorder induced by trauma or intraocular surgery.

In some embodiments, a scaffold described herein is implanted into the inner layer of the cornea of a subject in need thereof according to surgical methods known in the art (e.g., using the DSEK technique). In other embodiments, a scaffold described herein is implanted into another area of the body, e.g., serving as a vascular tissue implant, etc. In some embodiments, the scaffold includes cells seeded thereon (e.g., CECs as described herein).

Corneal implantation methods can include full thickness trepanation (PK) and deep keratectomy. In the PK method, full thickness corneal button is obtained using a trephine, and the corneal endothelial cell layer is replaced by a scaffold (seeded with CECs), resulting in a full thickness cornea to attach for the recipient. Specifically, the method can be carried out as follows. First, incision of the full thickness cornea of a recipient (host) is carried out by using a trephine, and apart (of the whole) of the cornea is collected as a button shape. Then, from the piece of cornea collected, the Descemet's membrane and a corneal endothelial cell layer are peeled off. The corneal implant is then attached to the exposed corneal stroma. Thereafter, the corneal graft is returned to the recipient and fixed with sutures.

For deep keratectomy, instead of extracting the full thickness of the cornea, only the deep portion of the cornea is excised. First, a part of the recipient's corneal stroma is delaminated, and the posterior part of corneal stroma and the Descemet's membrane or the endothelial cell layer are excised. Typically, only the endothelial cell layer or only the endothelial cell layer and Descemet's membrane are peeled and excised. Next, the scaffold seeded with CECs is inserted into the excised portion by using a spatula. If desired, air is pumped into the anterior chamber to aid in attaching the implant to the recipient cornea. To immobilize the scaffold, an adhesive such as a fibrin glue, fibronectin and the like may be used on demand. Where necessary, the air may be injected into the anterior chamber to immobilize the graft.

The preparation of the present invention preferably remains attached to the Descemet's membrane or corneal stroma at least for 3 days post-transplantation, and may be detached after day 3. For early detachment of the substrate, for example, the amount of the adhesive such as a fibrin glue, fibronectin and the like can be controlled. Moreover, a biodegradable material may be used for the substrate in the preparation of the present invention, so that the substrate will disappear after contact with the Descemet's membrane or corneal stroma for a predetermined period (e.g., at least 3 days). In this way, an improved postoperative QOV and earlier recovery of the visual acuity are expected. With the preparation of the present invention, viable adhesion of the corneal endothelial layer occurs in living organisms even when the substrate is detached, and the viably adhered cells can grow in the body. Therefore, the substrate does not need to be maintained at a transplantation site for a long time. The substrate that fell off in the anterior chamber can be removed within a given period after confirmation of the detachment. Even after early removal of the substrate, the cornea maintains transparency, and the recipient is basically expected to lead a normal life by around 2 weeks post-transplantation.

In addition, since the preparation of the present invention permits in vivo proliferation of the viably adhered cells, if may cover about 10-90%, preferably about 10-50%, more preferably about 20-40%, of the area of the disordered corneal endothelium. Since a small preparation can minimize the size of a cut, postoperative inflammation is mild and the possibility of postoperative infection can be decreased simultaneously.

Whether or not the transplanted corneal endothelial cell layer has a barrier function and a pump function as does the corneal endothelial cell layer in living organisms can be confirmed by, for example, examining the changes of corneal thickness and the development of edema after transplantation.

Accordingly, the present invention also provides a method of transplanting the composition of the present invention to a patient to cover an area smaller than a disordered corneal endothelium. Moreover, the present invention comprises a step of transplanting the preparation of the present invention to a patient, wherein said preparation remains attached to the Descemet's membrane or corneal stroma at least for 3 days after transplantation, and thereafter (1) detaches itself or (2) loses the substrate.

While the shape of the transparent hydrogel scaffold is not particularly limited as long as it can carry a corneal endothelial cell layer and is suitable for transplantation, a sheet form is preferable. In the preferred embodiment, the transparent hydrogel scaffold is a sheet of a thickness of 100-300 μm. When the preparation of the present invention is a sheet, it can be used after cutting into a size suitable for the application site during the transplantation. In addition, the sheet may be rolled small and inserted from a cut. A preferable specific example thereof is a disc shape covering about 30% of the area of a disordered corneal endothelium. It is also preferable to make a cut in a part surrounding the aforementioned disc shape, preferably toward the center, to allow close adhesion to the application site.

The preparation of the present invention is a corneal endothelial preparation comprising a transparent hydrogel scaffold and a cultured corneal endothelial cell layer, wherein the cultured corneal endothelial cells are those cultured in vitro. Specifically, as the cultured corneal endothelial cells, (1) those cultured at least in a culture vessel (e.g., culture dish, culture tube, culture tank etc.), (2) such cells passage-cultured further (preferably, 3-10 passages), or (3) such passage-cultured cells that are further cultured on a substrate, are used.

The cultured corneal endothelial cell layer contained in the preparation of the present invention has at least one of the following characteristics. It preferably has two or more, more preferably all of the following characteristics. (1) The cell layer has a monolayer structure. This is one of the characteristics of the corneal endothelial cell layer of living organisms. (2) The cell density of the cell layer is about 1,000-about 4,000 cells/mm$^2$. Particularly, when the recipient (transplantee) is an adult, the density is preferably about 2,000-about 3,000 cells/mm$^2$. (3) The visual flat plane shape of the cell constituting the cell layer is approximately hexagonal. This is one of the characteristics of the cell constituting the corneal endothelial cell layer in living organisms. The preparation of the present invention is similar to the corneal endothelial cell layer of living organisms, and exhibits a function similar to that of the inherent corneal endothelial cell layer, as well as an ability to proliferate in living organisms. (4) In the cell layer, cells are regularly aligned. In the corneal endothelial cell layer in living organisms, the cells constituting the layer are regularly aligned, by which it is considered that the corneal endothelial cells maintain normal function and high transparency and the cornea appropriately controls the water content. Having such morphological characteristics, the preparation of the present invention is expected to show functions similar to those of the corneal endothelial cell layer in living organisms.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Transparent Gelatin Hydrogel Cultured with Human Corneal Endothelial Cells In order to get a very flat gelatin hydrogel sheet, a two-step experiment was carried out in the first step, Gelatine type A film was prepared by pouring gelatin solution into a Petri dish and drying 2 days at room temperature. Secondly, gelatin film was cross-linked by 1-Ethyl-3-[3-dimethylaminopropyl] carbodiimide hydrochloride (EDC)/N-hydroxysuccinimide (NHS) in PBS solution at pH 5.0. The transparency, mechanical property and the microstructure of gelatine hydrogel were characterized respectively by UV-spectrophotometer, Instron, and scanning electron microscopy (SEM). The water content of gelatine hydrogel was measured at 37° C. in PBS solution, hydrogel's biodegradability was tested in PBS and collagenase aqueous solutions, respectively, and permeability of gelatin hydrogel was evaluated using two molecular weight of FITC-Dextrans (4 Kd and 70 Kd). Human corneal endothelial cells (hCEC) isolated from discarded donor corneas were seeded on the gelatin hydrogel and cell attachment and proliferation on the gelatin hydrogel were examined by microscopy and haematoxylin and eosin (H&E) staining.

A transparent gelatin hydrogel sheet was obtained by the cross-linking of gelatin, film with EDC/NHS. The thickness of sheet was in the range of 100-300 um, which meets the requirement of clinic application for corneal endothelial cells transfer. The gelatin sheet has a proper mechanical strength and flexibility, ensuring the hydrogel sheet is easily handled during the surgical implantation. The mechanical property of gelatin hydrogel is greatly influenced by the cross-linking time and the amount of cross-linking agent. After an 8 hr reaction, a stable gelatin hydrogel sheet was formed. Upon increasing the molar ratio between EDC and gelatin's amine from 2.5 to 10.0, the modulus of hydrogel increased from 0.1 MPa to 5.8 MPa, while the tensile strain of hydrogel decreased from about 250% to 50%. Gelatin hydrogel shows a high transparency, 95% within the visible light scope SEM results show that the gelatin hydrogel has a porous structure with a pore size of 20-30 um. The porous structure of gelatin hydrogel is helpful for the diffusion of nutrients and metabolites between cornea and anterior chamber. The water content of gelatin hydrogel is about 70-80%, which is very close to that of natural cornea stromas. Gelatin hydrogel was biodegradable and it was degraded completely when soaked in 21.6 U/ml of collagenase type I for several hours at 37° C. However in PBS solution, gelatin hydrogel was stable without obvious mass loss within one month. The permeability of gelatin hydrogel to 4K FITC-Dextran was greater than that of 70K FITC-Dextran. The gelatin hydrogel has a high biocompatibility, and hCEC cells can attach and proliferate on the hydrogel. hCEC cells were seeded directly on gelatin hydrogel, and after several days culture, a tight confluent cell layer was formed on the surface of hydrogel. This study indicates that gelatin hydrogel cross-linked with EDC/NHS is a promising scaffold for the transplantation of corneal endothelium.

Example 2: Modifications of Gelatin Hydrogel

Figure 2:
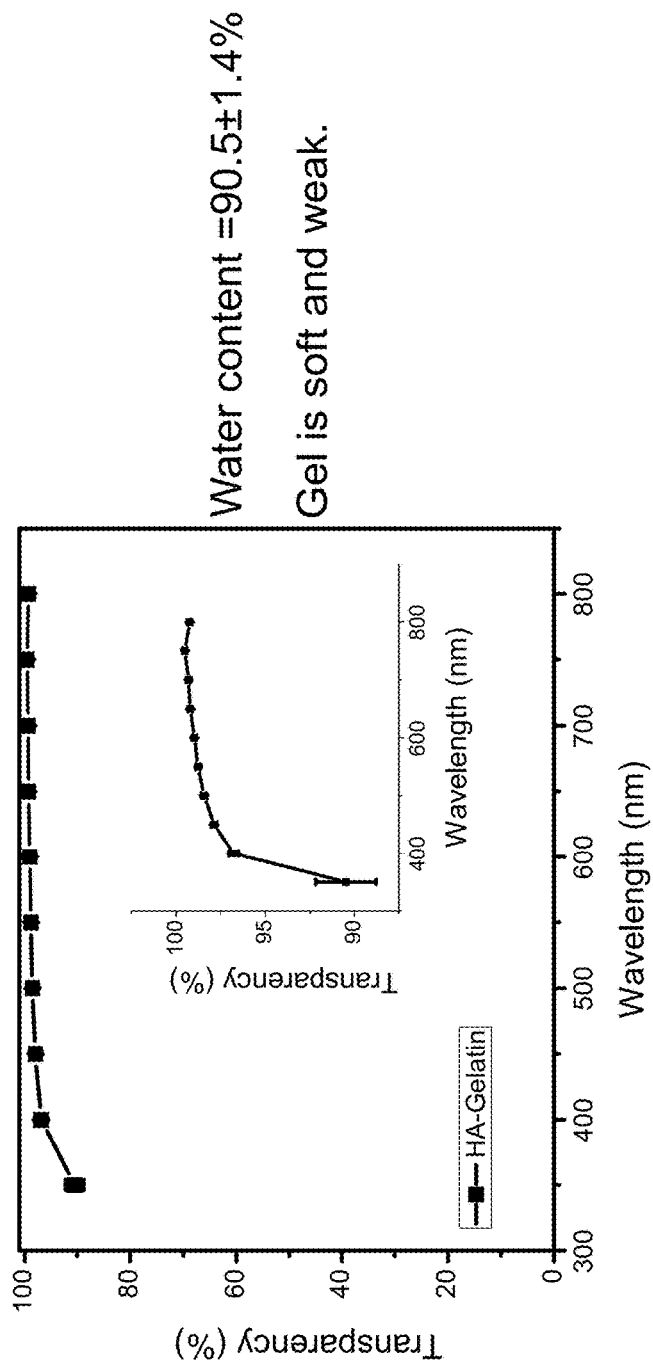
FIG. 2 is an image depicting the transparency of the HA-gelatin hydrogel in the visible light spectrum.

The transparent hydrogel can also comprise other polymer structures, along with gelatin. Hyaluronan (HA) is a biopolymer which can be polymerize with gelatin to form a scaffold containing both HA and gelatin (FIG. 1). As shown in FIG. 2, there is high transparency of this scaffold in the visible light spectrum, and a water content of 90.5%.

Figure 3:
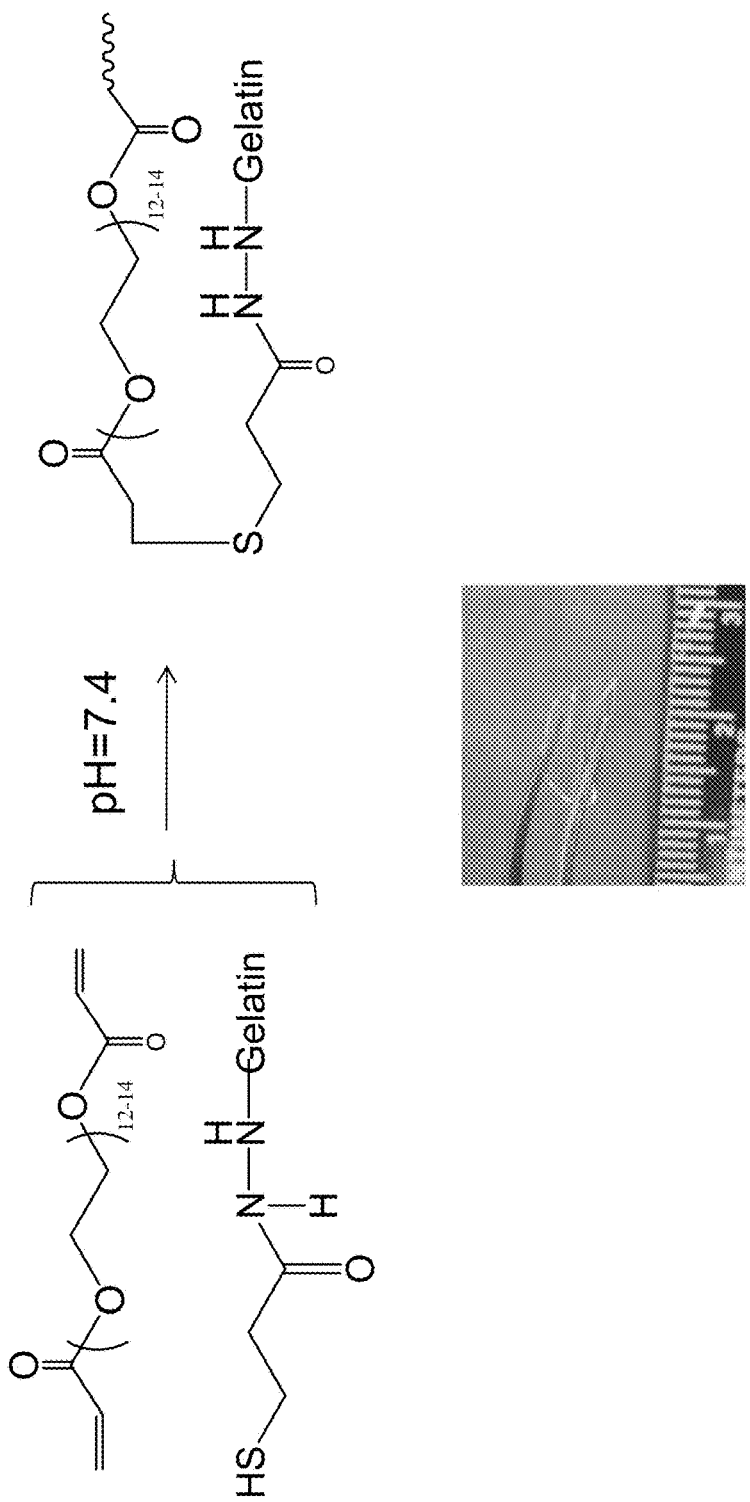
FIG. 3 is an image depicting the association of the biopolymer gelatin with the synthetic polymer poly(ethylene glycol) diacrylate (PEGDA) in the formation for a hydrogel comprising both polymers. An image of the resultant hydrogel scaffold is also shown.
Figure 4:
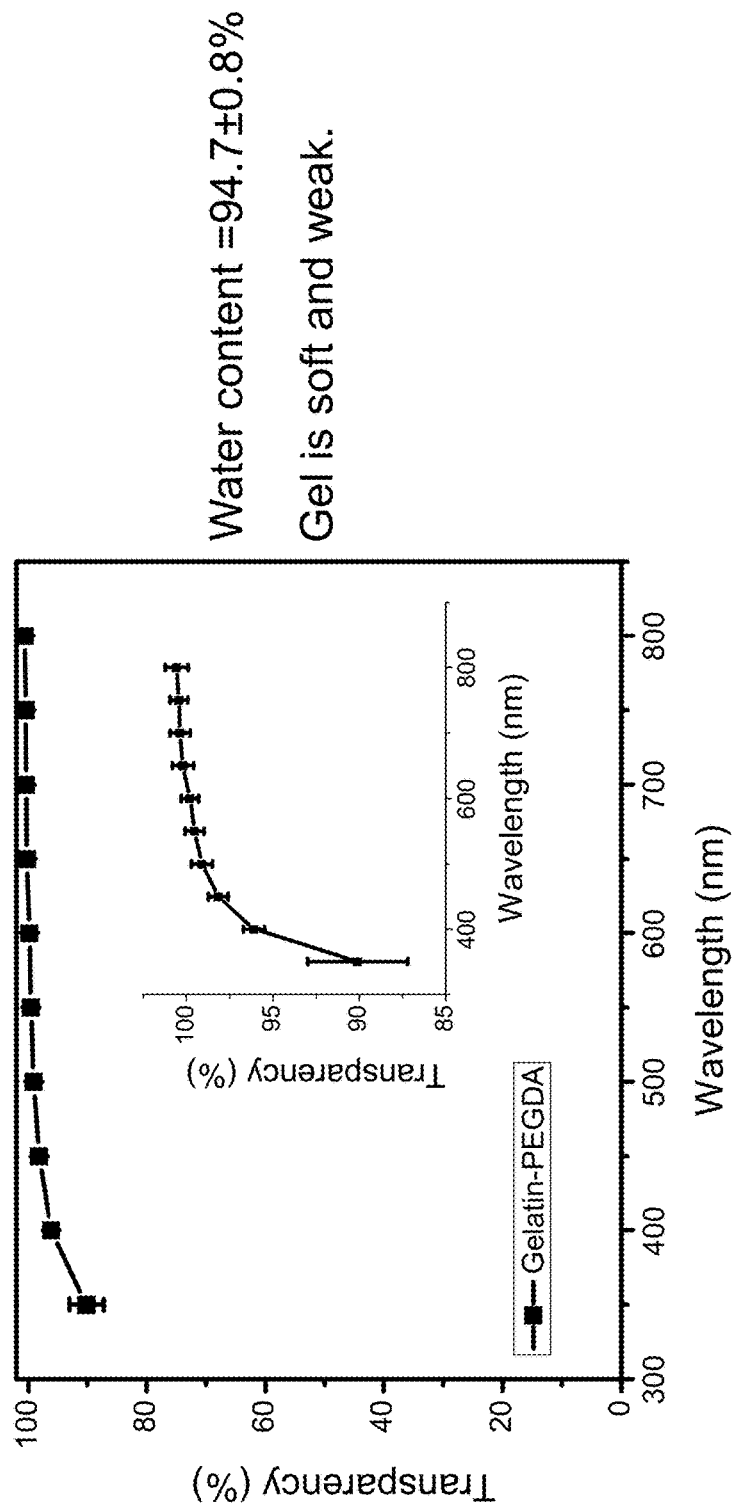
FIG. 4 is an image depicting the transparency of the Gelatin-PEGDA hydrogel in the visible light spectrum.

Alternatively, the hydrogel can comprise gelatin along with a synthetic polymer, including poly(ethylene glycol) diacrylate (PEGDA) (FIG. 3). Hydrogels comprising gelatin and PEGDA are also transparent and have a water content of 94.7% (FIG. 4).

Figure 5:
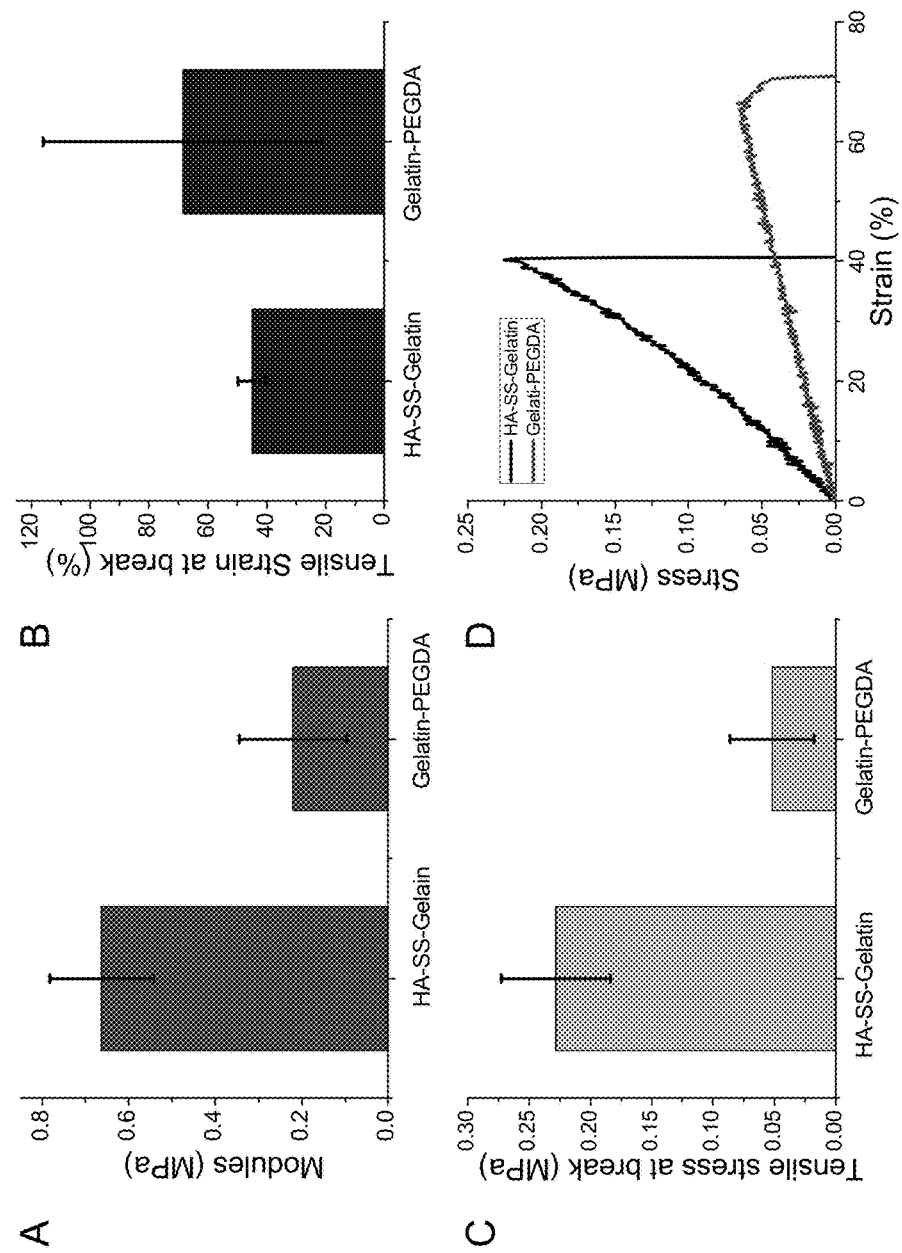
FIG. 5, comprising

Scaffolds comprising gelatin and HA, and scaffolds comprising gelatin and PEGDA were tested for their mechanical properties, where gelatin-HA hydrogels showed to have a greater modulus and tensile strength at break, compared to gelatin-PEGDA hydrogels (FIG. 5).

Figure 6:
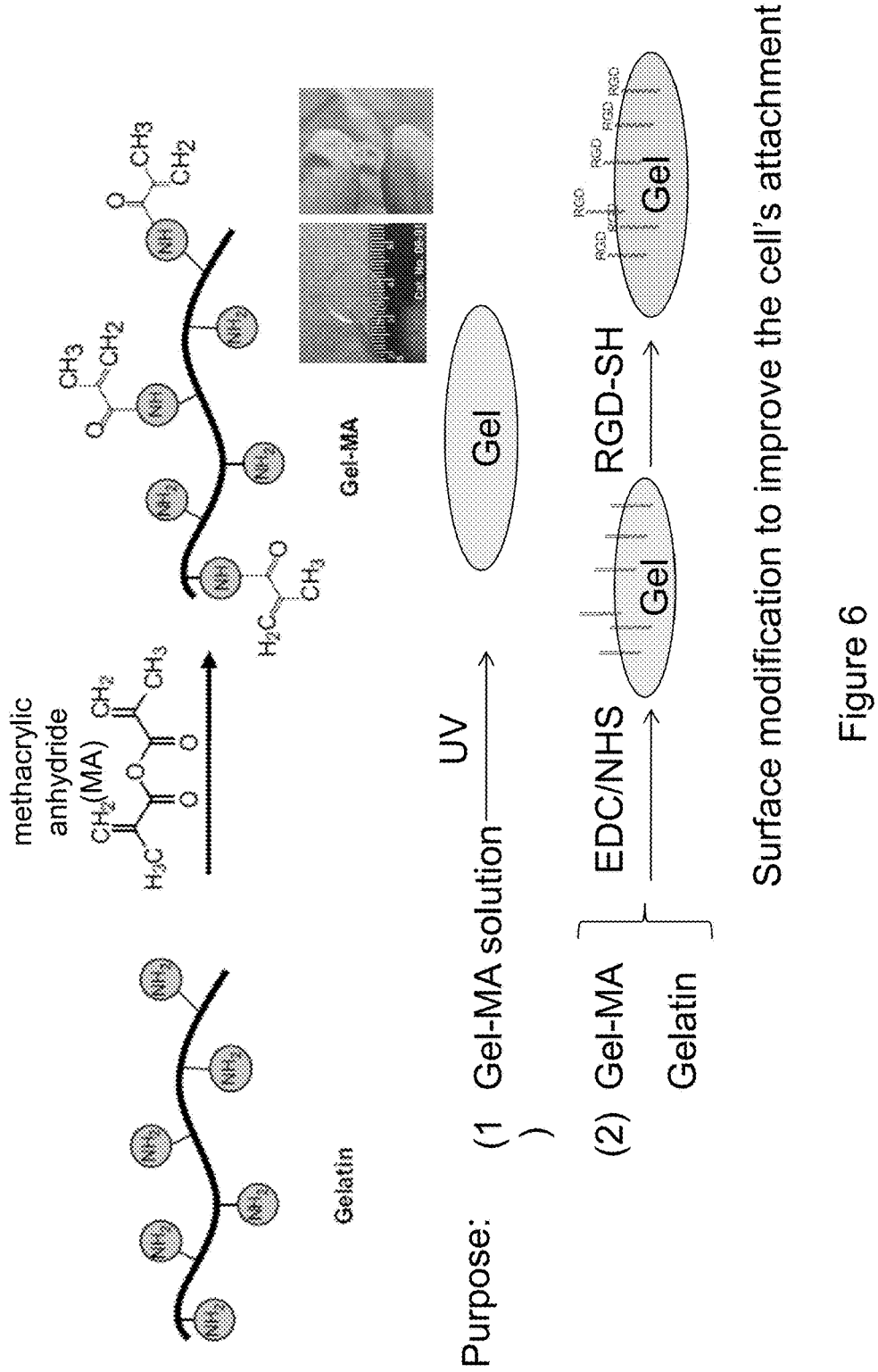
FIG. 6 is an image depicting the modification of gelatin by methacrylic anhydride (MA) to form Gelatin methacrylate (Gel-MA).

Hydrogels can also comprise gelatin that has been modified. Gelatin was treated with methyarcylic anhydride (MA) to produce gelatin methacrylate (Gel-MA) (FIG. 6). Gel-MA solution is polymerized into a gel with the application of UV light. Further, hydrogels can comprise both Gel-MA and unmodified gelatin, using chemical cross-linking agents EDC and NHS. These types of hydrogels can be further modified with the addition of RGD motifs within the hydrogel. These RGD motifs are surface modifications that can improve the cell attachment (FIG. 6).

Example 3: Heparin Modified Gelatin Gel

Figure 7:
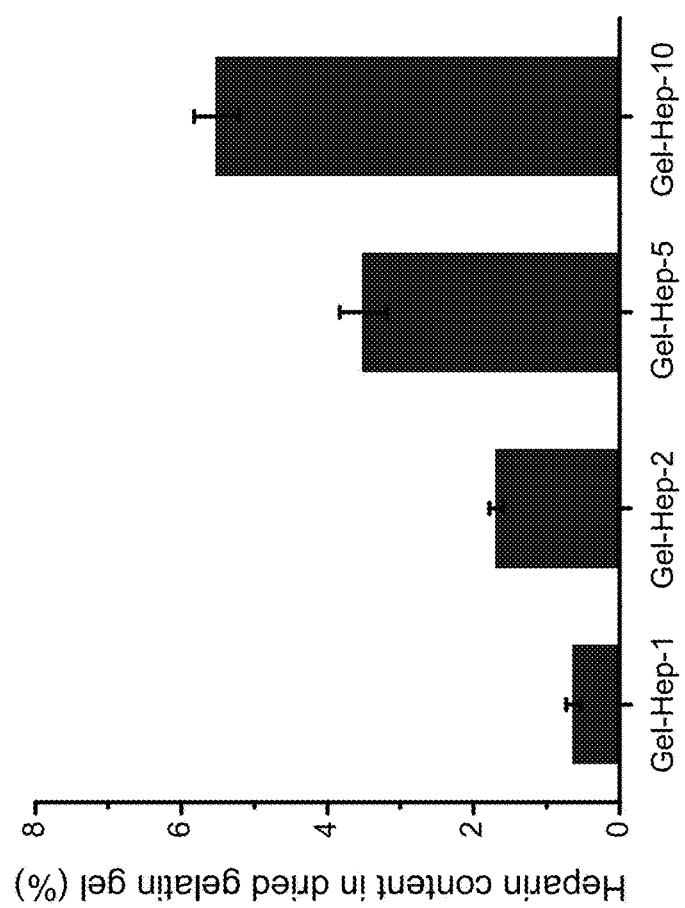
FIG. 7 is a graph illustrating the measured heparin content in various compositions of dried heparin modified gelatin gels. Gelatin gels were modified with the addition of 1% heparin (Gel-Hep-1), 2% heparin (Gel-Hep-2), 5% heparin (Gel-Hep-5), or 10% heparin (Gel-Hep-10).

In these set of experiments, it was examined whether various concentrations of heparin, incorporated into a gelatin gel, can influence the viability of hCECs cultured on the heparin modified gelatin gels. For these studies, four different compositions were constructed: Gel-Hep-1, Gel-Hep-2, Gel-Hep-5 and Gel-Hep-10, corresponding to the addition of 1, 2, 5, and 10% heparin, respectively, during gel preparation. The heparin content of each composition was measured. As shown in FIG. 7, an increase in the heparin content was observed as the amount of heparin added to the gel is increased.

Figure 8:
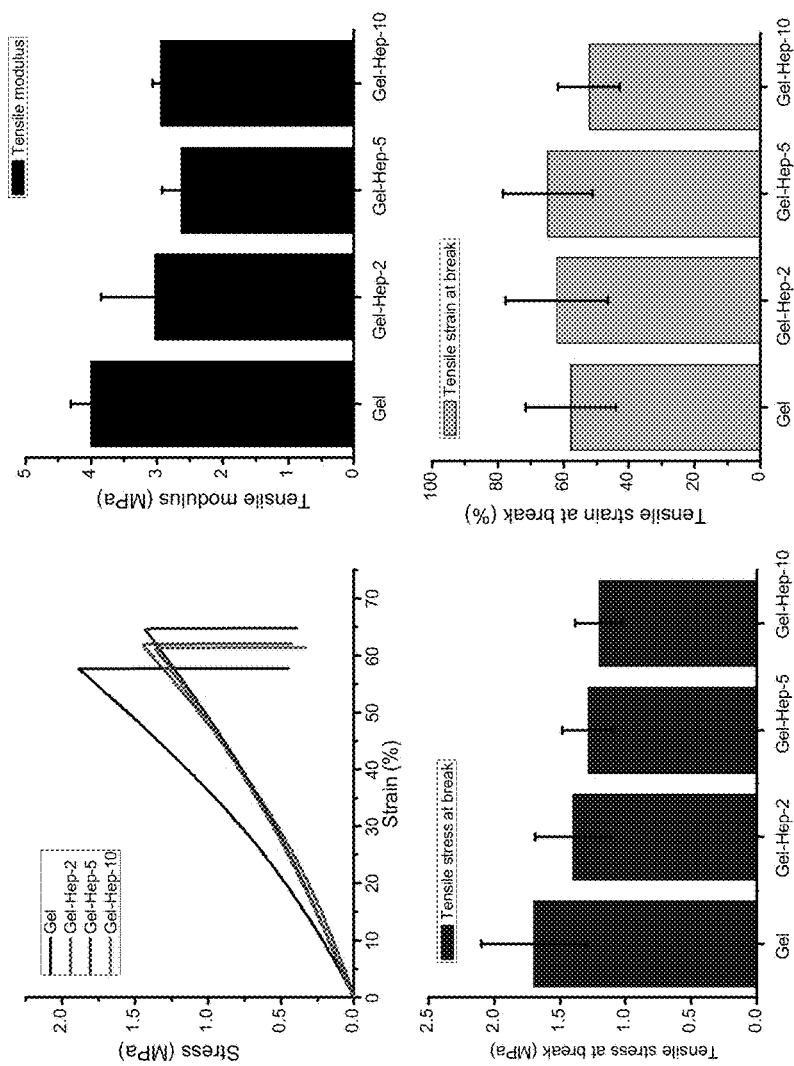
FIG. 8 is a set of graphs illustrating the mechanical properties of heparin modified gelatin gels, Gel-Hep-2, Gel-Hep-5, and Gel-Hep-10 compositions were compared with unmodified gel as a control. Depicted are stress-strain curves, tensile modulus, tensile stress at break, and tensile strain at break for each composition.

The mechanical properties of the heparin modified gel compositions were evaluated. FIG. 8, shows a stress-strain curve as well as mean values of tensile modulus, tensile stress at break, and tensile strain at break for unmodified gels, and for gels modified with either 2, 5, or 10% heparin. As depicted in FIG. 8, the scaffold stiffness and strength is decreased with increases in heparin content.

Figure 9:
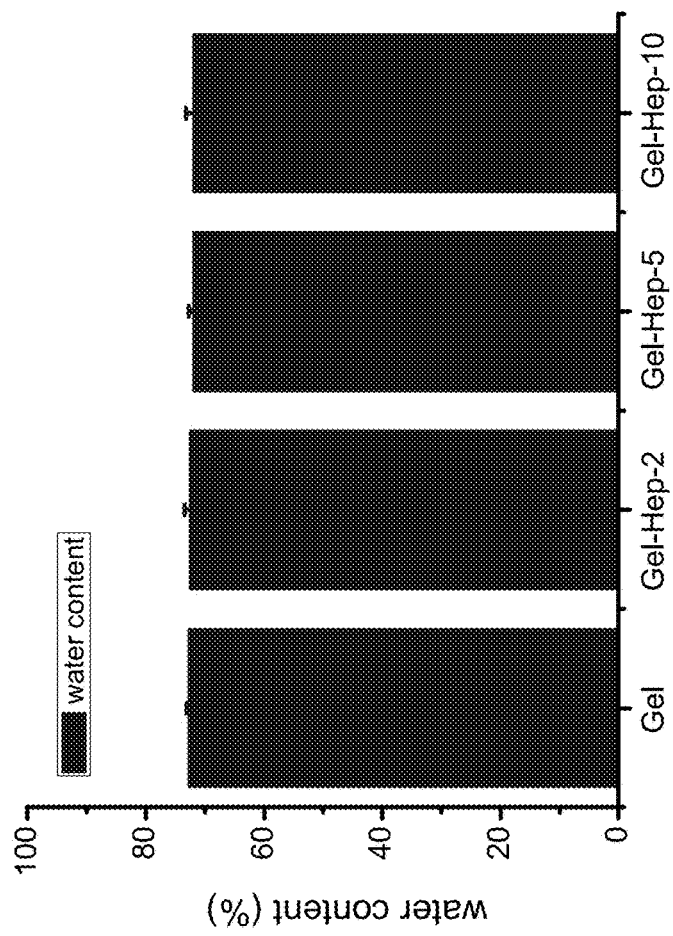
FIG. 9 is a graph illustrating the measured water content of heparin modified gelatin gels

Next, die water content of unmodified gelatin gels and gelatin gels modified with either 2, 5, or 10% heparin was measured. As shown in FIG. 9, the water content of the scaffold compositions did not change upon the addition of heparin.

The heparin modified gelatin gel compositions were evaluated for their ability to support hCEC growth. In these experiments, hCECs (h411, P4) were cultured on the gel compositions at an initial density of 50 cells/mm$^2$. Cells were cultured in DMEM with either 2% FBS or 10% FBS.

Figure 10:
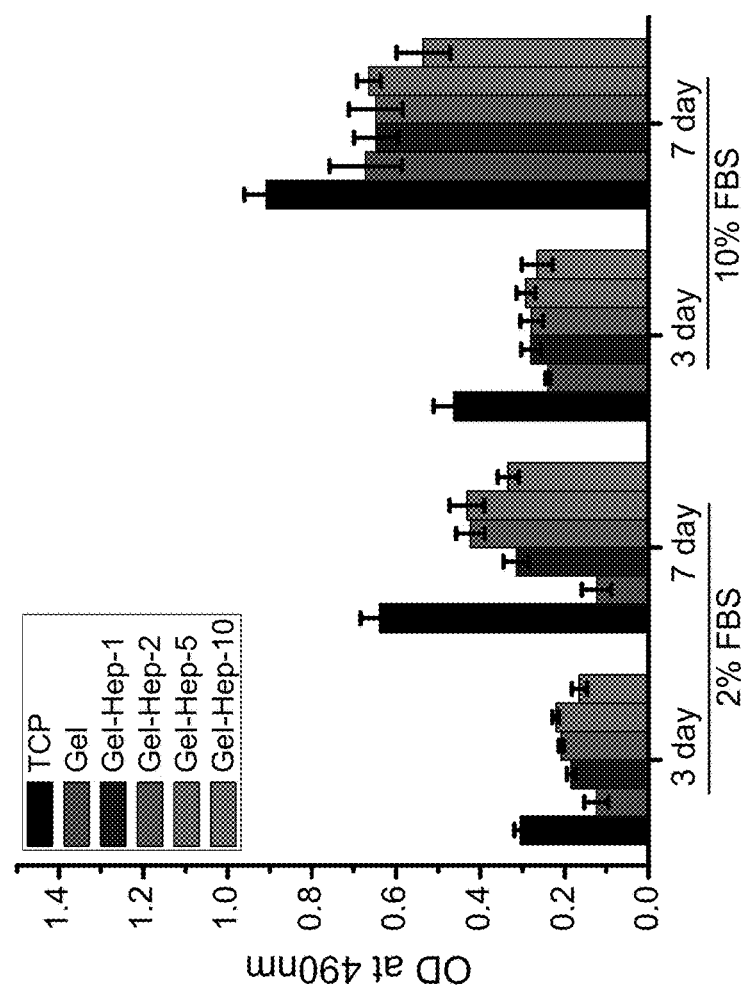
FIG. 10 is a graph illustrating the extent of hCEC growth on heparin modified gels, as compared to tissue culture plate and unmodified gels, hCECs were grown in either 2% or 10% FBS. Proliferation was measured using an MTS assay, where the absorbance at 490 mm is indicative of viable cell number.
Figure 11:
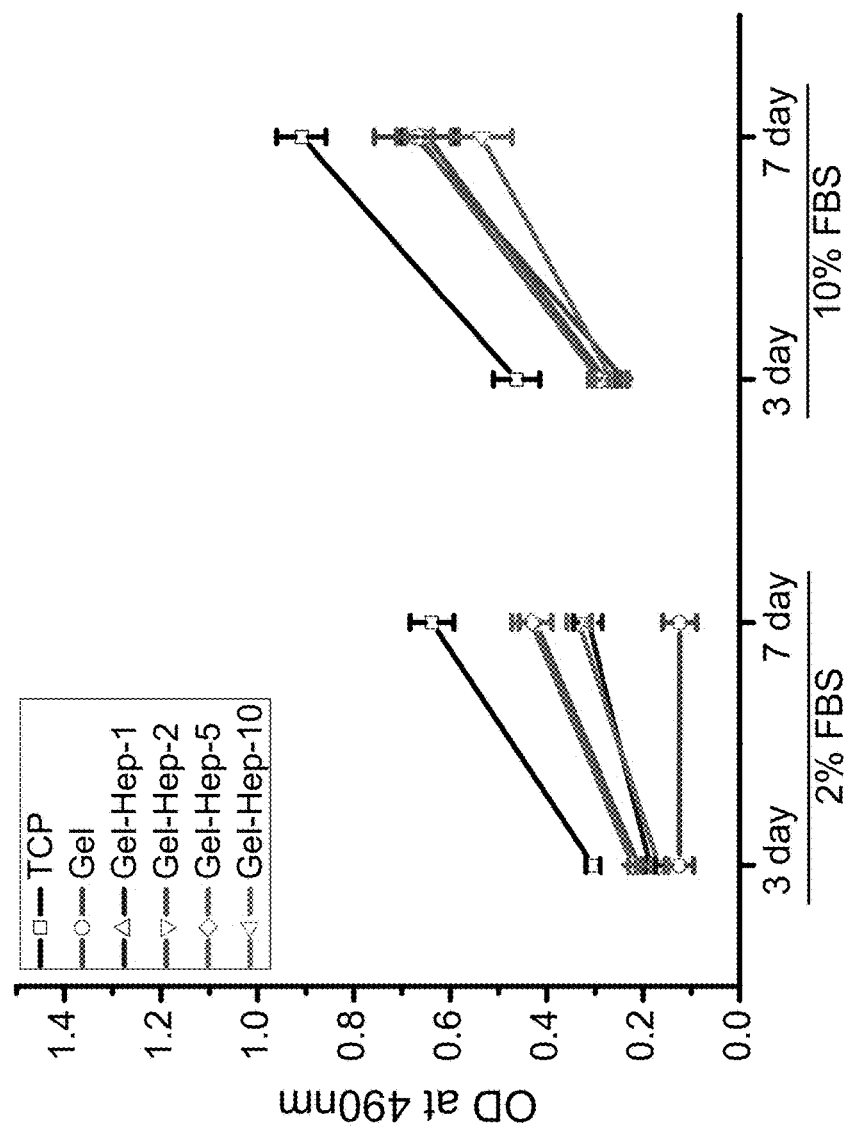
FIG. 11 is a graph illustrating the extent of hCEC growth on heparin modified gels, as compared to tissue culture plate and unmodified gels, hCECs were grown in either 2% or 10% FBS. Proliferation was measured using an MTS assay, where the absorbance at 490 mm is indicative of viable cell number.

An MTS assay was used to evaluate the cell growth on the heparin modified gelatin gel compositions. In this assay, [3-(4,5-dimethylthiazol-2-yl)-5-(3-carboxymethoxyphenyl)-2-(4-sulfophenyl)-2H-tetrazolium, inner salt; MTS] is added to the culture. MTS produces a formazan product that has an absorbance maximum at 490-500 nm. This assay measures cellular metabolic activity, which reflects the number of viable cells and thus cell proliferation in the present model. As shown in FIG. 10 and FIG. 11, analysis of the MTS assay demonstrates that incorporation of heparin increases the cell proliferation of cultured hCECs grown in 2% FBS. This increase is demonstrated at both 3 and 7 days. Further, in all heparin modified gel compositions, the number of viable cells was increased at 7 days compared to 3 days (FIG. 11), demonstrating the sustained proliferation of cultured hCECs in these constructs.

Figure 12:
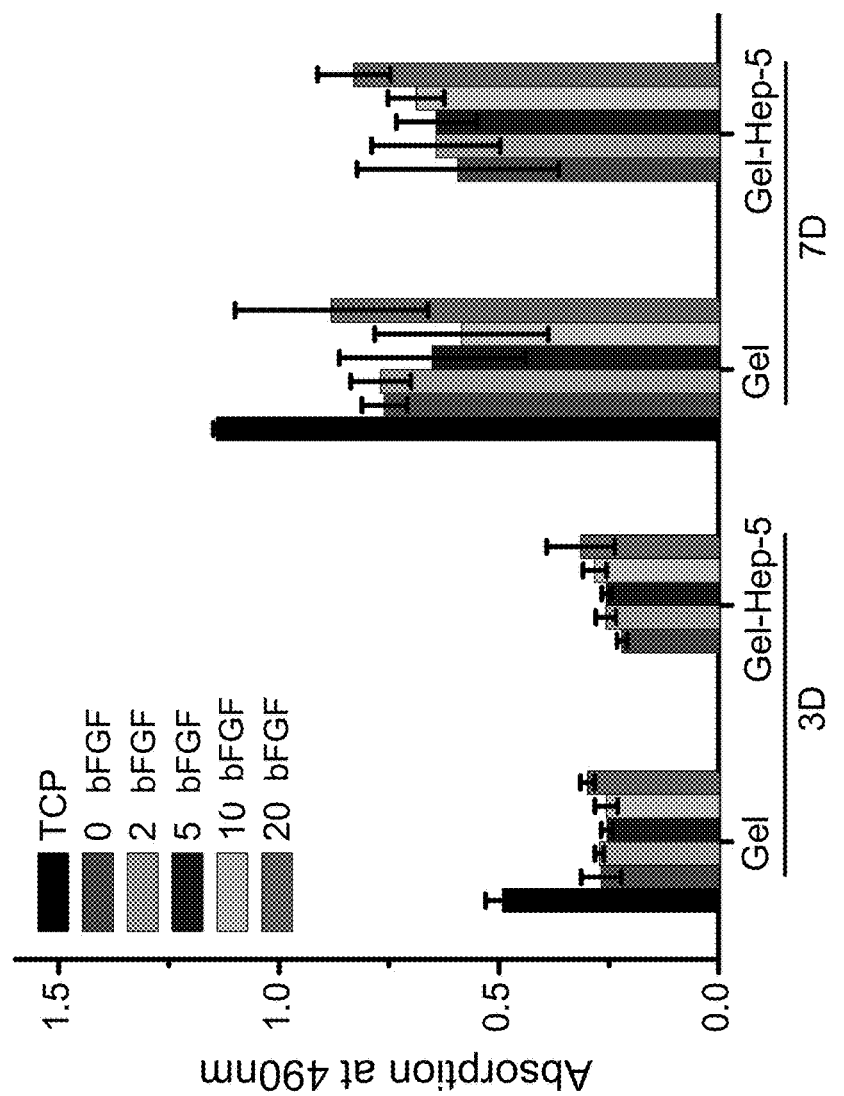
FIG. 12 is a graph illustrating the effect of bFGF on hCEC growth, when cultured on unmodified gelatin gels and gelatin gels modified with 5% heparin. Proliferation, was measured using an MTS assay, where the absorbance at 490 mm is indicative of viable cell number.

Next, the effect of the addition of bFGF on hCEC cell growth and proliferation when cultured on heparin modified gelatin gels was examined. Unmodified gelatin gels and gels modified with 5% heparin were treated with 0, 2, 5, 10, or 20 bFGF. As shown in FIG. 12, the addition of bFGF only induced an increase in cell growth on heparin modified gels.

The disclosures of each and every patent, patent application, and publication cited herein are hereby incorporated herein by reference in their entirety. While this invention has been disclosed with reference to specific embodiments, if is apparent that other embodiments and variations of this invention may be devised by others skilled in the art without departing from the true spirit and scope of the invention. The appended claims are intended to be construed to include all such embodiments and equivalent variations.

What is claimed:

1. A corneal endothelial composition comprising a transparent hydrogel scaffold modified with heparin and a layer of corneal endothelial cells present on the surface of the hydrogel scaffold, wherein the hydrogel scaffold is modified with an amount of heparin that enhances proliferation of the corneal endothelial cells on the hydrogel scaffold;
   wherein the hydrogel scaffold comprises and is cross-linked with 1-ethyl-3-[3-dimethylaminopropyl]carbodiimide hydrochloride (EDC), and N-hydroxysuccinimide (NHS);
   wherein the hydrogel scaffold comprises gelatin; and
   wherein the transparent hydrogel scaffold is formed by drying a solution comprising gelatin in a mold at room temperature.

2. The composition of claim 1, wherein the hydrogel scaffold further comprises at least one synthetic polymer, wherein the synthetic polymer is selected from the group consisting of (meth)acrylate-oligolactide-PEO-oligolactide-(meth)acrylate, poly(ethylene glycol) (PEO), poly(propylene glycol) (PPO), PEO-PPO-PEO copolymers, poly(phosphazene), poly(methacrylates), poly(N-vinylpyrrolidone), PL(G)A-PEO-PL(G)A copolymers, poly(ethylene imine), and poly(ethyl glycol) diacrylate.

3. The composition of claim 1, wherein gelatin is modified with methacrylic anhydride to form gelatin methacrylate.

4. The composition of claim 1, wherein the corneal endothelial cells are obtained from donor cornea.

5. A method of making the corneal endothelial composition of claim 1, the method comprising generating a thin hydrogel scaffold by drying a solution comprising gelatin in a mold at room temperature, adding both EDC and NHS to the hydrogel scaffold, crosslinking the hydrogel sheet with the EDC and NHS and culturing corneal endothelial cells on the surface of the hydrogel scaffold, wherein the hydrogel scaffold comprises heparin and is transparent.

6. The method of claim 5, wherein the hydrogel scaffold further comprises at least one synthetic polymer, wherein the synthetic polymer is selected from the group consisting of (meth)acrylate-oligolactide-PEO-oligolactide-(meth)acrylate, poly(ethylene glycol) (PEO), poly(propylene glycol) (PPO), PEO-PPO-PEO copolymers (Pluronics), poly(phosphazene), poly(methacrylates), poly(N-vinylpyrrolidone), PL(G)A-PEO-PL(G)A copolymers, poly(ethylene imine), and poly(ethyl glycol) diacrylate.

7. The method of claim 5, wherein the gelatin is modified with methacrylic anhydride to form gelatin methacrylate.

8. The method of claim 5, wherein the corneal endothelial cells are obtained from donor cornea.

9. The method of claim 5, wherein the corneal endothelial cells are cultured in the presence of basic fibroblast growth factor (bFGF).

10. The composition of claim 1, wherein the composition has a size of about 10-90% of corneal endothelium.

11. The composition of claim 1, wherein the hydrogel scaffold is in the range of about 100-300 µm thick.

12. A corneal endothelial composition comprising a transparent hydrogel scaffold modified with heparin and a layer of corneal endothelial cells present on the surface of the hydrogel scaffold, wherein the hydrogel scaffold comprises gelatin, is cross-linked with, 1-ethyl-3-[3-dimethylaminopropyl]carbodiimide hydrochloride (EDC), and N-hydroxysuccinimide (NHS), and wherein the hydrogel scaffold is modified with an amount of heparin that enhances proliferation of the corneal endothelial cells on the hydrogel scaffold;

wherein the hydrogel scaffold comprises at least one synthetic polymer, wherein the synthetic polymer is selected from the group consisting of (meth)acrylate-oligolactide-PEO-oligolactide-(meth)acrylate, poly(ethylene glycol) (PEO), poly(propylene glycol) (PPO), PEO-PPO-PEO copolymers, poly(phosphazene), poly(methacrylates), poly(N-vinylpyrrolidone), PL(G)A-PEO-PL(G)A copolymers, poly(ethylene imine), and poly(ethyl glycol) diacrylate; and wherein the transparent hydrogel scaffold is formed by drying a solution comprising gelatin in a mold at room temperature.

\* \* \* \* \*